US008653026B2

(12) United States Patent
Ma (10) Patent No.: US 8,653,026 B2
(45) Date of Patent: Feb. 18, 2014

(54) TREATMENT OF TYPE 2 DIABETES WITH FTY720

(71) Applicant: Diapin Therapeutics LLC, Ann Arbor, MI (US)

(72) Inventor: Zhonigman Ma, Ann Arbor, MI (US)

( * ) Notice: Subject to any disclaimer, the term of this patent is extended or adjusted under 35 U.S.C. 154(b) by 0 days.

(21) Appl. No.: 13/722,495

(22) Filed: Dec. 20, 2012

(65) Prior Publication Data

US 2013/0123172 A1    May 16, 2013

Related U.S. Application Data

(63) Continuation of application No. PCT/US2012/049565, filed on Aug. 3, 2012.

(60) Provisional application No. 61/574,441, filed on Aug. 3, 2011.

(51) Int. Cl.
*A61K 31/135* (2006.01)
*A61K 31/137* (2006.01)
*A61K 45/06* (2006.01)

(52) U.S. Cl.
USPC ............................. 514/6.7; 514/6.9; 514/104

(58) Field of Classification Search
None
See application file for complete search history.

(56) References Cited

U.S. PATENT DOCUMENTS

| | | | |
|---|---|---|---|
| 5,604,229 | A | 2/1997 | Fujita et al. |
| 5,719,176 | A | 2/1998 | Fujita et al. |
| 5,952,316 | A | 9/1999 | Fujita et al. |
| 6,004,565 | A | 12/1999 | Chiba et al. |
| 7,015,218 | B1 | 3/2006 | Ushio et al. |
| 2004/0023885 | A1* | 2/2004 | Brand et al. ............ 514/12 |
| 2004/0209801 | A1* | 10/2004 | Brand et al. ............ 514/12 |
| 2005/0227954 | A1* | 10/2005 | Suzuki et al. .......... 514/177 |
| 2006/0183674 | A1* | 8/2006 | Brand et al. ............ 514/11 |
| 2009/0176744 | A1* | 7/2009 | Liu et al. ............... 514/114 |

FOREIGN PATENT DOCUMENTS

EP    0990440 A1    4/2000

OTHER PUBLICATIONS

Definition of analog, from http://cancerweb.ncl.ac.uk/omd/about.html, pp. 1-5. Accessed Jul. 7, 2005.*
Han, H.-K.. AAPS Pharmsci., 2000, 2(1), article 6, pp. 1-11.*
Muller, Christa E. "Prodrug Approaches for Enhancing the Bioavailability of Drugs with Low Solubility," Chemistry & Biodiversity, 2009, vol. 6, pp. 2071-2083.*
Ettmayer P. et al. J. Med. Chem. 2004, 47(10), pp. 2393-2404.*
Testa Prodrug research: futile or fertile? Biochemical Pharmacology, 2004, 2097-2106.*
Beaumont, et, al "Design of Ester Prodrugs to Enhance Oral Absorption of Poorly Permeable Compounds: Challenges to the Discovery Scientist," Current Drug Metabolism, 2003, 4, 461-485.*
Efficacy and safety of Fingolimod (FTY720) in Patients with Relapsing-remitting Multiple Sclerosis (Freedoms II), from ClinicalTrials.gov, pp. 1-4. Accessed Aug. 2, 2013.*
American Diabetes Association: "Diagnosis and classification of diabetes mellitus", Diabetes Care, 2006, vol. 29, Suppl. 1 pp. s43-s48.
Jorns A. et al, "Diabetes Prevention by Immunomodulatory FTY720 Treatment in the LEW.1AR1-iddm Rat Despite Immune Cell Activation", Endocrinology, 2010, vol. 151, No. 8, pp. 3555-3565.
Kendall M. R. et al, "FTY720, a sphingosine-1-phosphate receptor modulator, reverses high-fat diet-induced weight gain, insulin resistance and adipose tissue inflammation in C57BL/6 mice", Diabetes Obesity and Metabolism, 2008, vol. 10, No. 9, pp. 802-805.
Maki T et al "Prevention of autoimmune diabetes by FTY720 in nonobese diabetic mice", Transplantation, 2002, vol. 74, No. 12, pp. 1684-1686.
Popovic J et al "The effect of immunomodulators on prevention of autoimmune diabetes is stage dependent: FTY720 prevents diabetes at three different stages in the diabetes-resistant biobreeding rat", Pediatric Diabetes, 2004 vol. 5, No. 1, pp. 3-9.
Zhao Z. et al ""FTY720 Normalizes Hyperglycemia by Stimulating β-Cell in Vivo Regeneration in db/db Mice through Regulation of Cyclin D3 and p57KIP2 "", Journal of Biological Chemistry, 2012, vol. 287, No. 8, pp. 5562-5573. First Published Dec. 22, 2011.
PCT/US2012/049565 International Search Report Dated Sep. 21, 2012.
National Institute of Neurological Disorders and Stroke, "Amyotrophic Lateral Sclerosis (ALS) Fact Sheet", NINDS. Publication date Mar. 2012
"Jessup, C. F., et al., ""The Sphingolipid Rheostat: a Potential Target for Improving Pancreatic Islet Survival and Function"", Endocrine, Metabolic & Immune Disorders—Drug Targets, 2011, vol. 11, No. 4."

* cited by examiner

*Primary Examiner* — Julie Ha
(74) *Attorney, Agent, or Firm* — Honigman Miller Schwartz and Cohn LLP; Cynthia M. Bott; Johnathan P. O'Brien

(57) ABSTRACT

Methods for prevention and treatment of type-2 diabetes comprising administering to the subject an effective amount of FTY-720 or an analog are described.

3 Claims, 10 Drawing Sheets

Figure 1

Sphingosine

FTY720

FTY720-P

TREATMENT OF TYPE 2 DIABETES WITH FTY720

CROSS-REFERENCE TO RELATED APPLICATION

This application is a continuation of PCT Application No. PCT/US2012/049565, filed on Aug. 3, 2012, which claims priority to U.S. Provisional Application Ser. No. 61/574,441, filed Aug. 3, 2011. The entire content of these applications are incorporated herein by reference.

STATEMENT OF FEDERAL SUPPORT

This invention was made with government support under grant number NS063962 awarded by the National Institute of Health. The government has certain rights in the invention.

FIELD

The present invention relates generally to the field of type-2 diabetes (T2D). More particularly, the present invention concerns method for treating prediabetes and for preventing and treating type T2D.

BACKGROUND OF THE INVENTION

Diabetes is a group of metabolic diseases characterized by high levels of blood glucose levels (≥126 mg/dL or 7.0 mmol/L). The three most common forms of diabetes are type-1 diabetes (T1D), type-2 diabetes (T2D), and gestational diabetes. T1D, also known as insulin-dependent diabetes mellitus (IDDM), is caused by the autoimmune destruction of insulin producing pancreatic beta-cells leading to total deficiency of insulin, requiring patients with T1D to take insulin by either injection or pump. Gestational diabetes is developed when pregnant women become intolerant to glucose. Gestational diabetes requires treatment to maintain appropriate blood glucose levels in order to avoid complications in the infant.

Nearly 25.8 million people in the United States have diabetes and T2D accounts for 90 to 95 percent of diagnosed diabetes. Diabetes is the leading cause of kidney failure, non-traumatic lower-limb amputation, and new cases of blindness among adults in the United States. People with diabetes are also two to four times more likely than people without diabetes to develop heart disease.

T2D, previously known as non-insulin-dependent diabetes mellitus (NIDDM), develops as peripheral cells do not use insulin properly and then the pancreas loses its ability to produce enough insulin. Under current criteria, T2D is diagnosed when fasting plasma glucose is ≥126 mg/dL (7.0 mmol/L); or plasma glucose level is ≥200 mg/dL (11.1 mmol/L) at 2-hours post-glucose load of 75 g; or an $A_1C$ level≥6.5%.

Prediabetes, also referred as impaired fasting glucose (IFG) or impaired glucose tolerance (IGT), is a precursor condition to T2D. Prediabetes is diagnosed when fasting plasma glucose is between 100 to 125 mg/dL (5.56-6.94 mmol/L); or plasma glucose level is between 140 to 199 mg/dL (7.78-11.06 mmol/L) at 2-hours post-glucose load of 75 g; or an $A_1C$ level between 5.7 and 6.4%. Without intervention and appropriate treatment, people with prediabetes are at risk for developing T2D.

Lysophospholipids (LPs), including lysophosphatidic acid (LPA) and sphingosine 1-phosphate (S1P), are a group of phospholipid-derived lipid mediators and have growth factor-like effects to stimulate cell proliferation and survival through a group of G-protein coupled receptors (GPCRs), known as S1P receptors (S1P1-5). Levels of LPs are significantly increased during human pregnancy, a physiological condition under which pancreatic beta-cell mass is expanded to produce enough insulin keeping blood glucose in a normal range. Therefore, an LP analog was screened in ex vivo islets and in the db/db mice for its ability of expanding beta-cell mass. The db/db mouse is a widely used T2D animal model that exhibits severe depletion of insulin-producing beta-cells of the pancreatic islets. In this invention, it is demonstrated that oral administration of FTY720 to db/db mice normalizes fasting blood glucose by increasing beta-cell mass and blood insulin levels without affecting insulin sensitivity.

FTY720 is derived from the myriocin (ISP-1) metabolite of the fungus Isaria sinclairii and originally proposed as an anti-rejection medication indicated after transplantation. It is a structural analog of sphingosine and in vivo is phosphorylated by sphingosine kinase II to form FTY720-phosphate (FTY720-P). S1P1 plays a key role in the immune system, regulating lymphocyte egress from lymphoid tissues into the circulation. Binding of FTY720-P to S1P1 down regulates and degrades the S1P1 in lymphocytes. Therefore, FTY720 can sequester lymphocytes in lymph nodes, preventing them from moving to the central nervous system for autoimmune responses in Multiple Sclerosis. At present, FTY720 (trade name GILENYA®, generic name fingolimod) is FDA approved and is marketed by Novartis for the treatment of patients with relapsing multiple sclerosis (MS). Loss of insulin-producing beta-cell mass is a central component in the pathogenesis of T2D. Pancreatic beta-cells can modulate their mass in response to a variety of physiological and pathophysiological cues. Although some anti-diabetic drugs may positively affect beta-cells, there are few effective therapeutic approaches proposed to target beta-cell mass expansion. Therefore, there is a need for effective drugs and therapeutic methods that can preserve and increase the mass of functional beta-cells in patients with prediabetes or T2D.

SUMMARY OF THE INVENTION

The present invention provides methods for treating prediabetes, preventing and treating T2D; treating poor glycemic control; and treating reduced insulin levels comprising administering to a patient in need thereof, an effective amount of FTY720, FTY-P, a pharmaceutically acceptable salt or ester of FTY720, or a pharmaceutically acceptable salt or ester of FTY720-P.

One embodiment of the invention is a method for treating a subject having prediabetes or type-2 diabetes comprising administering to the subject, a composition comprising an effective amount of FTY720 or a pharmaceutically acceptable salt or ester thereof. Another embodiment is a method for treating a subject having prediabetes or type-2 diabetes comprising administering to the subject, a composition comprising an effective amount of FTY720-P or a pharmaceutically acceptable salt or ester thereof.

Another embodiment is a method for preserving or increasing the mass of functional beta-cells in a subject having prediabetes or type-2 diabetes comprising administering to the subject, a composition comprising an effective amount of FTY720 or a pharmaceutically acceptable salt or ester thereof. Yet another embodiment is a method for preserving or increasing the mass of functional beta-cells in a subject having prediabetes or type-2 diabetes comprising administering to the subject, a composition comprising an effective amount of FTY720-P or a pharmaceutically acceptable salt or ester thereof.

Another embodiment is a method for increasing insulin levels in a subject having prediabetes or type-2 diabetes comprising administering to the subject, a composition comprising an effective amount of FTY720 or a pharmaceutically acceptable salt or ester thereof. Another embodiment is a method for increasing insulin levels in a subject having prediabetes or type-2 diabetes comprising administering to the subject, a composition comprising an effective amount of FTY720-P or a pharmaceutically acceptable salt or ester thereof.

One embodiment of the invention is a method for treating a subject having poor glycemic control comprising administering to the subject, a composition comprising an effective amount of FTY720 or a pharmaceutically acceptable salt or ester thereof. Another embodiment disclosure is a method for treating a subject having poor glycemic control comprising administering to the subject, a composition comprising an effective amount of FTY720-P or a pharmaceutically acceptable salt or ester thereof.

BRIEF DESCRIPTION OF THE DRAWING

The following drawings form part of the present specification and are included to further demonstrate the aspect of the present invention. The invention can be better understood by reference to one or more of these drawings in combination with the detailed description of specific embodiments presented herein.

FIG. 2A. Time course of the fasting glucose levels of db/db mice with or without oral FTY720. Open circle (○), FTY720-untreated group; solid circle (●), pre-diabetic db/db mice (Fasting glucose<126 mg/dL) at six-week-old treated with 10 mg/kg FTY720; and triangle (▲), diabetic db/db mice (Fasting glucose≅430 mg/dL) at nine-week-old treated with 10 mg/kg FTY720 (n=4). I, Fasting glucose of mice at the age of 6 weeks to 12 weeks at the daily dosage of 10 mg/kg FTY720 (n=20 for the control and FTY720 treated pre-diabetic mice, respectively); II, fasting glucose levels of mice at the age of 12 weeks to 20 weeks at the daily dosage of 10 mg/kg FTY720 (n=6 for the control and FTY720 treated mice, respectively); III, fasting glucose levels of mice at the age of 20 weeks to 29 weeks at the weekly dosage of 10 mg/kg FTY720 (n=2 for control and FTY720 treated mice, respectively); IV, fasting glucose levels from the mouse without FTY720 treatment after age of 29 weeks (n=2 for control and FTY720 treated mice, respectively).

FIG. 2B. Time course of the body weight of db/db mice with or without oral FTY720. Open circle (○), FTY720-untreated group; solid circle (●), pre-diabetic db/db mice (Fasting glucose<126 mg/dL) at six-week-old treated with 10 mg/kg FTY720. I, body weight of mice at the age of 6 weeks to 12 weeks at the daily dosage of 10 mg/kg FTY720 (n=20 for the control and FTY720 treated pre-diabetic mice, respectively); II, body weight of mice at the age of 12 weeks to 20 weeks at the daily dosage of 10 mg/kg FTY720 (n=6 for the control and FTY720 treated mice, respectively); III, body weight of mice at the age of 20 weeks to 29 weeks at the weekly dosage of 10 mg/kg FTY720 (n=2 for control and FTY720 treated mice, respectively); IV, body weight from the mouse without FTY720 treatment after age of 29 weeks (n=2 for control and FTY720 treated mice, respectively).

DETAILED DESCRIPTION OF THE INVENTION

Definitions

FTY720, fingolimod, and GILENYA® (fingolimod) are names for the compound of formula (I)

(I)

which has the chemical name: 2-amino-2-[2-(4-octylphenyl) ethyl]propane-1,3-diol.

FTY720, fingolimod, GILENYA® and 2-amino-2-[2-(4-octylphenyl)ethyl]propane-1,3-diol are used interchangeably herein.

Fingolimod is phosphorylated in vivo by the action of sphingosine kinase to form fingolimod-phosphate; an active metabolite of fingolimod. Fingolimod-phosphate has the structure of formula (II)

which has the chemical name: 2-amino-2-(hydroxymethyl)-4-(4-octylphenyl)butyl dihydrogen phosphate.

Fingolimod-phosphate, FTY720-P and 2-amino-2-(hydroxymethyl)-4-(4-octylphenyl)butyl dihydrogen phosphate are used interchangeably herein.

Subject as used herein refers to warm blooded animals such as, for example, guinea pigs, mice, rats, gerbils, cats, rabbits, dogs, monkeys, chimpanzees, stump tail macques, and humans.

As used herein, the singular forms "a", "an" and "the" include plural references unless the context clearly dictates otherwise.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

As used herein "pharmaceutically acceptable" means suitable for use in mammals.

As used herein "salts" refer to pharmaceutically acceptable salts and to salts suitable for use in industrial processes, such as the preparation of the compound.

Figure 1:
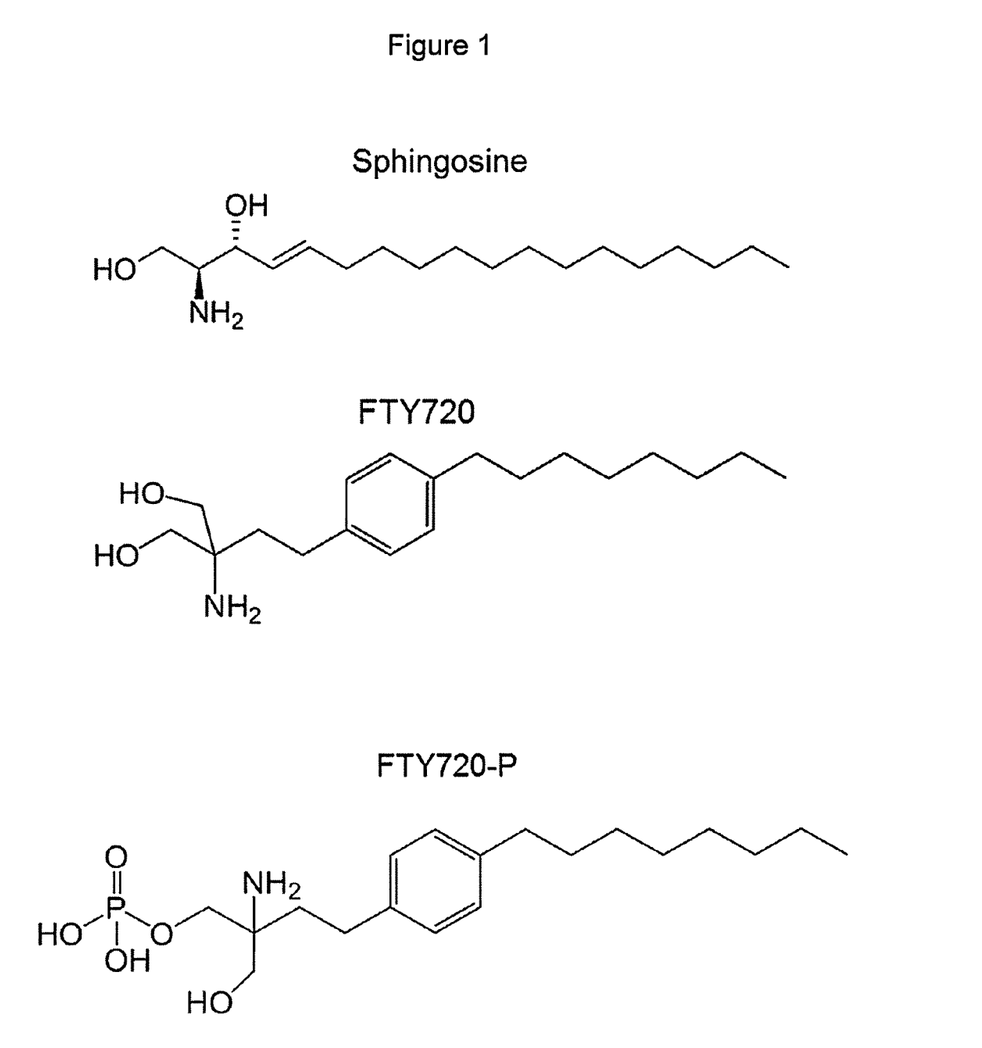
FIG. 1. Provides the chemical structures of sphingosine, FTY720 and FTY720-P.

Loss of functional insulin-producing beta-cell mass is a key event in the pathogenesis of T2D. Preserving and increasing beta-cell mass is considered as a potentially curative therapy for treating T2D. Pancreatic beta-cells can modulate their mass in response to a variety of physiological (pregnancy) and pathophysiological (obesity or insulin resistance) states. Since LPs have growth factor-like effects and are elevated during pregnancy, a physiological condition with beta-cell mass expansion, the PL analog FTY720 was screened using db/db mice, a widely used T2D mouse model. FTY720, the structure of which is shown in FIG. 1, an analog of sphingosine, was identified to be capable of normalizing the fasting glucose levels when FTY720 was i.p. injected into or orally administrated to db/db mice.

There are several advantages of the present invention. First, FTY720 is a FDA approved medicine for the treatment of patients with relapsing multiple sclerosis (MS) and its safety profile has been well studied during the clinical trial for treatment of relapsing MS, including more than 4,500 patient years of experience, with some patients in their seventh year of treatment. Second, FTY720 is an orally taken therapy and easy to take by patients, compared with insulin and GLP-1 analog therapies that have to be injected into body either by healthcare professionals or by patients themselves. Third, the well-controlled fasting glucose levels over time occurred despite the fact that FTY720 administration was ceased completely, indicating that FTY720 therapy is long lasting and has potential to cure T2D. Finally, although FTY720 promotes beta-cell regeneration, the risk of tumorigenesis is low. Concentrations of FTY720 identical to those used in this study (10 mg/kg) reportedly inhibit the growth, migration, and invasion of pancreatic cancer cells. The compound has also been used in phase III clinical trials in patients with relapsing multiple sclerosis without reported cancer formation. During the course of this invention, no cancer formation was observed.

Exemplary Embodiments of the Invention

An embodiment of the invention is a method for treating a subject having prediabetes or type-2 diabetes, comprising administering to the subject, a composition comprising an effective amount of FTY720 or a pharmaceutically acceptable salt or ester thereof, or FTY720-P or a pharmaceutically acceptable salt or ester thereof.

An embodiment of the invention is a method for treating a subject having prediabetes comprising administering to the subject, a composition comprising an effective amount of FTY720 or a pharmaceutically acceptable salt or ester thereof. Another embodiment of the invention is a method for treating a subject having type-2 diabetes comprising administering to the subject, a composition comprising an effective amount of FTY720 or a pharmaceutically acceptable salt or ester thereof. Yet another embodiment of the invention is a method for preventing type-2 diabetes in a subject having prediabetes comprising administering to the subject, a composition comprising an effective amount of FTY720 or a pharmaceutically acceptable salt or ester thereof. An embodiment of the invention is a method for treating a subject having prediabetes comprising administering to the subject, a composition comprising an effective amount of FTY720 or a pharmaceutically acceptable salt thereof. Another embodiment of the invention is a method for treating a subject type-2 diabetes comprising administering to the subject, a composition comprising an effective amount of FTY720 or a pharmaceutically acceptable salt thereof. Yet another embodiment of the invention is a method for preventing type-2 diabetes in a subject having prediabetes comprising administering to the subject, a composition comprising an effective amount of FTY720 or a pharmaceutically acceptable salt.

An embodiment of the invention is a method for treating a subject having prediabetes comprising administering to the subject, a composition comprising an effective amount of FTY720-P or a pharmaceutically acceptable salt or ester thereof. Another embodiment of the invention is a method for treating a subject having type-2 diabetes comprising administering to the subject, a composition comprising an effective amount of FTY720-P or a pharmaceutically acceptable salt or ester thereof. Yet another embodiment of the invention is a method for preventing type-2 diabetes in a subject having prediabetes comprising administering to the subject, a composition comprising an effective amount of FTY720-P or a pharmaceutically acceptable salt or ester thereof.

An embodiment of the invention is a method for treating a subject having prediabetes comprising administering to the subject, a composition comprising an effective amount of FTY720-P or a pharmaceutically acceptable salt. Another embodiment of the invention is a method for treating a subject having type-2 diabetes comprising administering to the subject, a composition comprising an effective amount of FTY720-P or a pharmaceutically acceptable salt. Yet another embodiment of the invention is a method for preventing type-2 diabetes in a subject having prediabetes, comprising administering to the subject, a composition comprising an effective amount of FTY720-P or a pharmaceutically acceptable salt.

An embodiment of the invention is a method for preserving or increasing the mass of functional beta-cells in a subject having prediabetes, comprising administering to the subject, a composition comprising an effective amount of FTY720 or a pharmaceutically acceptable salt or ester thereof, or FTY720-P or a pharmaceutically acceptable salt or ester thereof.

An embodiment of the invention is a method for preserving the mass of functional beta-cells in a subject having prediabetes, comprising administering to the subject, a composition comprising an effective amount of FTY720 or a pharmaceutically acceptable salt or ester thereof. An embodiment of the invention is a method for preserving the mass of functional beta-cells in a subject having prediabetes comprising administering to the subject, a composition comprising an effective amount of FTY720 or a pharmaceutically acceptable salt thereof.

An embodiment of the invention is a method for preserving the mass of functional beta-cells in a subject having prediabetes comprising administering to the subject, a composition comprising an effective amount of FTY720-P or a pharmaceutically acceptable salt or ester thereof. An embodiment of the invention is a method for preserving the mass of functional beta-cells in a subject having prediabetes comprising administering to the subject, a composition comprising an effective amount of FTY720-P or a pharmaceutically acceptable salt thereof.

Another embodiment is a method for preserving the mass of functional beta-cells in a subject having type-2 diabetes comprising administering to the subject, a composition comprising an effective amount of FTY720-P or a pharmaceutically acceptable salt or ester thereof. An embodiment of the invention is a method for preserving the mass of functional beta-cells in a subject having type-2 diabetes comprising administering to the subject, a composition comprising an effective amount of FTY720-P or a pharmaceutically acceptable salt thereof.

An embodiment of the invention is a method for increasing the mass of functional beta-cells in a subject having prediabetes comprising administering to the subject, a composition comprising an effective amount of FTY720 or a pharmaceutically acceptable salt or ester thereof. Another embodiment of the invention is a method for increasing the mass of functional beta-cells in a subject having prediabetes comprising administering to the subject, a composition comprising an effective amount of FTY720 or a pharmaceutically acceptable salt thereof.

An embodiment of the invention is a method for increasing the mass of functional beta-cells in a subject having type-2 diabetes comprising administering to the subject, a composition comprising an effective amount of FTY720 or a pharmaceutically acceptable salt or ester thereof. Another embodiment of the invention is a method for increasing the mass of functional beta-cells in a subject having type-2 diabetes comprising administering to the subject, a composition comprising an effective amount of FTY720 or a pharmaceutically acceptable salt thereof.

Yet another embodiment of the invention is a method for or increasing the mass of functional beta-cells in a subject having prediabetes comprising administering to the subject, a composition comprising an effective amount of FTY720-P or a pharmaceutically acceptable salt or ester thereof. An embodiment of the invention is a method for or increasing the mass of functional beta-cells in a subject having prediabetes comprising administering to the subject, a composition comprising an effective amount of FTY720-P or a pharmaceutically acceptable salt thereof.

Yet another embodiment of the invention is a method for or increasing the mass of functional beta-cells in a subject having type-2 diabetes comprising administering to the subject, a composition comprising an effective amount of FTY720-P or a pharmaceutically acceptable salt or ester thereof. An embodiment of the invention is a method for or increasing the mass of functional beta-cells in a subject having type-2 diabetes comprising administering to the subject, a composition comprising an effective amount of FTY720-P or a pharmaceutically acceptable salt thereof.

An embodiment of the invention is a method for increasing insulin levels in a subject having prediabetes or type-2 diabetes comprising administering to the subject, a composition comprising an effective amount of FTY720 or a pharmaceutically acceptable salt or ester thereof or FTY720-P or a pharmaceutically acceptable salt or ester thereof.

An embodiment of the invention is a method for increasing insulin levels in a subject having prediabetes comprising administering to the subject, a composition comprising an effective amount of FTY720 or a pharmaceutically acceptable salt or ester thereof. An embodiment of the invention is a method for increasing insulin levels in a subject having prediabetes comprising administering to the subject, a composition comprising an effective amount of FTY720 or a pharmaceutically acceptable salt thereof.

An embodiment of the invention is a method for increasing insulin levels in a subject having prediabetes comprising administering to the subject, a composition comprising an effective amount of FTY720-P or a pharmaceutically acceptable salt or ester thereof. An embodiment of the invention is a method for increasing insulin levels in a subject having prediabetes comprising administering to the subject, a composition comprising an effective amount of FTY720-P or a pharmaceutically acceptable salt thereof.

An embodiment of the invention is a method for increasing insulin levels in a subject having type-2 diabetes comprising administering to the subject, a composition comprising an effective amount of FTY720 or a pharmaceutically acceptable salt or ester thereof. An embodiment of the invention is a method for increasing insulin levels in a subject having type-2 diabetes comprising administering to the subject, a composition comprising an effective amount of FTY720 or a pharmaceutically acceptable salt thereof.

An embodiment of the invention is a method for increasing insulin levels in a subject having type-2 diabetes comprising administering to the subject, a composition comprising an effective amount of FTY720-P or a pharmaceutically acceptable salt or ester thereof. An embodiment of the invention is a method for increasing insulin levels in a subject having type-2 diabetes comprising administering to the subject, a composition comprising an effective amount of FTY720-P or a pharmaceutically acceptable salt thereof.

One embodiment of the invention is a method for treating a subject having poor glycemic control comprising administering to the subject, a composition comprising an effective amount of FTY720 or a pharmaceutically acceptable salt or ester thereof. Another embodiment disclosure is a method for treating a subject having poor glycemic control comprising administering to the subject, a composition comprising an effective amount of FTY720-P or a pharmaceutically acceptable salt or ester thereof. Yet another embodiment of the invention is a method for treating a subject having poor glycemic control comprising administering to the subject, a composition comprising an effective amount of FTY720 or a pharmaceutically acceptable salt thereof. Another embodiment disclosure is a method for treating a subject having poor glycemic control comprising administering to the subject, a composition comprising an effective amount of FTY720-P or a pharmaceutically acceptable salt thereof.

In some of the embodiments of the invention the subject having prediabetes has a fasting plasma glucose level between 100 to 125 mg/dL. In other embodiments of the invention the subject having prediabetes has a plasma glucose level between 140 to 199 mg/dL at 2-hours post-glucose load of 75 g. In some of the embodiments of the invention the subject having prediabetes has an $A_1C$ level between 5.7 and 6.4%.

In some of the embodiments of the invention the subject having type-2 diabetes has a fasting plasma glucose level≥126 mg/dL. In some of the embodiments of the invention the subject having type-2 diabetes has a plasma glucose level≥200 mg/dL at 2-hours post-glucose load of 75 g. In some of the embodiments of the invention the subject having type-2 diabetes has a an $A_1C$ level≥6.5%.

Formulations, Administrations, and Uses

In another aspect, the invention includes a pharmaceutical composition comprising a FTY-720, or a pharmaceutically acceptable salt thereof, and a pharmaceutically acceptable carrier or adjuvant.

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. In some embodiments, the prodrugs increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Currently FTY720 is marketed for treatment of relapsing multiple sclerosis under the trade name as GILENYA® (fingolimod) which is administered orally. However, FTY720 may also be formulated to be administered by other means which are well known in the art. For example, the compositions of the present invention may be administered orally, parenterally, by inhalation spray, topically, rectally, nasally, buccally, or via an implanted reservoir. One of skill in the art is well versed in formulation of therapeutic agents. See e.g. *Remington*: The Science and Practice of Pharmacy, 20th Edition, Lippincott Williams & White, Baltimore, Md. (2000); *Remington's Pharmaceutical Sciences*, 19th Edition (Mack Publishing Company, 1995). *Remington's* Pharmaceutical Sciences, 18th ed., Gennaro, A R. Ed., Mack Publishing, Easton Pa. (1990)

The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene-polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

The amount of the compounds of the present invention that may be combined with the carrier materials to produce a composition in a single dosage form (unit dose) will vary depending upon the host treated and the particular mode of administration. In some embodiments, the compositions should be formulated so that a dosage of between about 0.0001 to about 10 mg/kg body weight/day of fingolimod is administered to a patient receiving these compositions. In some embodiments the dosage is between about 0.0001 to about 1 mg/kg/day. In other embodiments the dosage is between about 0.0001 to about 5 mg/kg/day. In other embodiments the dosage is between about 0.0005 to about 1 mg/kg/day. In other embodiments the dosage is between about 0.001 to about 1 mg/kg/day. In yet other embodiments the dosage is between about 0.001 to about 0.5 mg/kg/day. In another embodiment the dosage is between about 0.001 and 0.05 mg/kg/day.

The unit dose in some embodiments is between about 0.001 mg to about 70 mg, or between about 0.01 mg to about 35 mg, or between about 0.1 mg to about 35 mg or between about 0.1 to about 5 mg, or about 0.1 to about 1 mg. The unit dose in some embodiments is 0.1 mg, or 0.2 mg, or 0.25 mg, or 0.3 mg, or 0.4 mg, or 0.5 mg, or 0.6 mg, or 0.7 mg, or 0.75 mg, or 0.8 mg, or 0.9 mg, or 1 mg, or 1.1 mg, or 1.2 mg, or 1.25 mg, or 1.5 mg, or 1.75 mg or 2 mg, or 2.5 mg or 3 mg, or 5 mg.

The compositions of the invention may be administered one or multiple times daily. For example in one embodiment the composition is administered once-daily. In another embodiment the composition is administered twice-daily. In yet another embodiment the composition is administered three-times daily. In another embodiment the composition is administered four-times daily.

One of ordinary skill in the art understands that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

FTY-720 may be administered with additional therapeutic agents, for example therapeutic agents which are normally administered to treat or prevent type-2 diabetes. In one embodiment the therapeutic agent is insulin. In some embodiments the drugs are administered in separate dosage forms. In other embodiments one or more additional therapeutic agent can be present in the compositions of this invention. Examples of therapeutic drugs that are used to treat prediabetes or type-2 diabetes include Biguanides including, but not limited to, Metformin (GLUCOPHAGE®, GLUCOPHAGE XR®, GLUMETZA®, RIOMET®, FORTAMET®); Meglitinides including, but not limited to Repaglinide (PRANDIN®), Nateglinide (STARLIX®); Sulfonylureas including, but not limited to, Chlorpropamide (DIABINESE®), Glimepiride (AMARYL®), Glipizide (GLUCOTROL®), Glyburide (DIABETA®, MICRONASE®, GLYNASE®), Tolazamide (TOLINASE®), Tolbutamide (ORINASE®); Thiazolidinediones (Glitazones) including but not limited to Pioglitazone (ACTOS®) and Rosiglitazone (AVANDIA®); Alpha Glucosidase Inhibitors including, but not limited to, Acarbose (PRECOSE®) and Miglitol (GLYSET®); Dipeptidyl Peptidase Inhibitors including, but not limited to, Sitagliptin (JANUVIA®) and Saxagliptin (ONGLYZA®); Ergot Alkaloids including, but not limited to bromocriptine (CYCLOSET®); Incretin mimetics, including, but not limited to, exenatide (BYETTA®) and liraglutide (VICTOZA®); amylin analogues, including, but not limited to pramlintide acetate (SYMLIN®); Combination Oral Diabetes Medications, including but not limited to, Glipizide and metformin (METAGLIP®), glyburide and metformin (GLUCOVANCE®), pioglitazone and glimepiride (DUETACT®), Pioglitazone and metformin (ACTOplus MET®), Repaglinide and metformin (PRANDIMET™), Rosiglitazone and glimepiride (AVANDARYL®), Rosiglitazone and metformin (AVANDAMET®), Sitagliptin and metformin (JANUMET®).

Some of the compounds of the disclosure will exist as optical isomers. Any reference in this application to one of the compounds is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively, utilization of a specific optical isomer as the starting material will produce the corresponding isomer as the final product.

Experimental Procedures

Animals and Procedures—Five-week-old female db/db mice (BKS.Cg-m+/−Leprdb) were purchased from Jackson Laboratories (Bar Harbor, Me.). Mice were housed under controlled light (12 h light/12 h dark) and temperature conditions, and had free access to food (normal rodent chow) and water. All procedures were conducted in accordance with the guidelines on Animal Care and were approved by the Institutional Animal Care and Use Committee (IACUC) of Mount Sinai School of Medicine. After 1 week, the fasting glucose levels of the 6-week-old mice were measured. Mice with normal glucose levels (<126 mg/dl) were randomly divided into control and FTY720 treatment groups. Mice in the FTY720-treated group were fed 10 mg/kg of FTY720 daily by feeding tube and their food intake and body weight were measured twice a week. Fasting glucose levels were measured at the end of each week. At 12 weeks of age (when the mice had been treated for 6 weeks), all mice were subjected to metabolic analysis. After metabolic analysis, the pancreases were removed from the mice at 13 and 16 weeks of age for immunohistochemical analysis, quantitation of islet area, or islet isolation.

Intraperitoneal Glucose Tolerance Test or Insulin Tolerance

For the glucose tolerance test, the mice were fasted for 16 h and intraperitoneally injected with 10% glucose (1 mg/g of body weight). Glucose levels were then measured after 0, 30, 60, 90, and 120 min by a Glucometer Elite (Bayer Corp., Elkhart, Ind.) (29). For the insulin tolerance test, the mice were fasted for 6 h and injected intraperitoneally with human regular insulin (0.55 units/kg) (Sigma). Tail blood samples were collected at 0, 30, 40, 60, 90, and 120 min for glucose measurement (30, 31).

Determination of Serum Insulin Levels

After overnight fasting, blood samples (50.1) were collected in a heparinized microhematocrit tube for the determination of insulin concentration using a Ultra Sensitive Mouse Insulin ELISA Kit (Crystal Chem Inc., Downers Grove, Ill.) (30).

Immunohistochemical Analysis

Pancreases were removed from the db/db mice, fixed overnight in 4% formaldehyde solution, and embedded in paraffin. Paraffin sections (10 µm thick) were rehydrated, and antigen retrieval in 10 mM sodium citrate solution was performed using a microwave, followed by blocking endogenous peroxidase in 3% $H_2O_2$ solution. The following primary antibodies were used: guinea pig anti-swine insulin (1:300; DAKO Corp., Carpinteria, Calif.), rabbit anti-glucagon (1:200; Thermo Fisher Scientific, Fremont, Calif.), mouse anticyclin D3 (1:40; Vector Laboratory, Burlingame, Calif.), mouse anti-BrdU (1:10; BD Biosciences), rabbit anti-Ki67 (1:100; Abcam, Cambridge, Mass.), and rabbit anti-p57KIP2 (1:100; Abcam, Cambridge, Mass.). Goat anti-mouse/rabbit IgG (Vector Laboratory) and goat anti-guinea pig-mouse/rabbit IgG conjugated with the ALEXA FLUOR® dyes (ALEXA FLUOR® 488 and ALEXA FLUOR®; Invitrogen) were used for the secondary antibodies. All images were captured by a Zeiss Axioplan 2 microscope (32, 33).

Assessment of Islet Areas

To assess islet area in pancreas after 6 weeks of treatment with FTY720, six consecutive paraffin sections (10 µm) from a pancreas (10 pancreases for the control and 9 pancreases for the FTY720-treated group) were used. All islet images on a whole section were taken by a Axioplan 2 microscope at X10 magnification, each islet area was measured by the Java-based image-processing program ImageJ (National Institutes of Health, Bethesda, Md.), and the sum of all islet areas from a section was considered to be the islet area per pancreas.

Islet Isolation and Cell Culture

Islets were isolated from pancreases removed from the 13-week-old untreated and FTY720-treated db/db mice by Liberase (Roche Diagnostics) digestion, followed by discontinuous Ficoll gradient separation and manual stereomicroscopic selection to exclude contaminating tissues (30). Isolated islets (or INS-1 cells) were cultured in the medium (composed of RPMI 1640 medium supplemented with 10% fetal bovine serum, 2 mM L-glutamine, 1% sodium pyruvate, 50 µM β-mercaptoethanol, 100 units/ml of penicillin, and 100 µg/ml of streptomycin). For treatment of INS-1 cells, the cells were plated in RPMI medium overnight and changed to Hanks' balanced salt solution containing 2 mM glucose and 0.5% FBS overnight. Then the cells were treated with various conditions in the same medium for 24 hours.

Measurement of β-Cell Regeneration In Vivo

After overnight fasting, the mice were given 1 mg/ml of 5-bromo-2-deoxyuridine (BrdU) in PBS intraperitoneally. Mice were sacrificed 24 hours after BrdU injection and pancreases were removed and fixed with a 4% formaldehyde solution. The pancreases were then embedded in paraffin and sliced into 10 µm sections. Tissue sections were stained with the anti-BrdU monoclonal antibody provided in BrdU in Situ Detection Kit (BD Biosciences).

EXAMPLES

Example 1

Oral Administration of FTY720 to db/db Mice Normalizes Hyperglycemia Without Affecting Insulin Sensitivity To rigorously determine the effects of FTY720 in vivo, pre-diabetic (age of six weeks, fasting glucose<126 mg/dL) and diabetic (age of 8-9 weeks, fasting glucose=430 mg/dL) female db/db mice were fed daily with FTY720 (+FTY720) for 29 weeks, and monitored by weekly fasting blood glucose measurements. It was demonstrated that the fasting glucose levels in the FTY720-treated pre-diabetic db/db mice remained normal (~126 mg/dL) and in diabetic db/db mice (glucose≥350 mg/dL) also became normal after six weeks of FTY720-treatment whereas fasting glucose levels increased significantly in the untreated group (−FTY720) by the age of eight weeks and continued to increase over time (to about 500 mg/dL by the age of 12 weeks) (FIG. 2A).

Figure 2A:
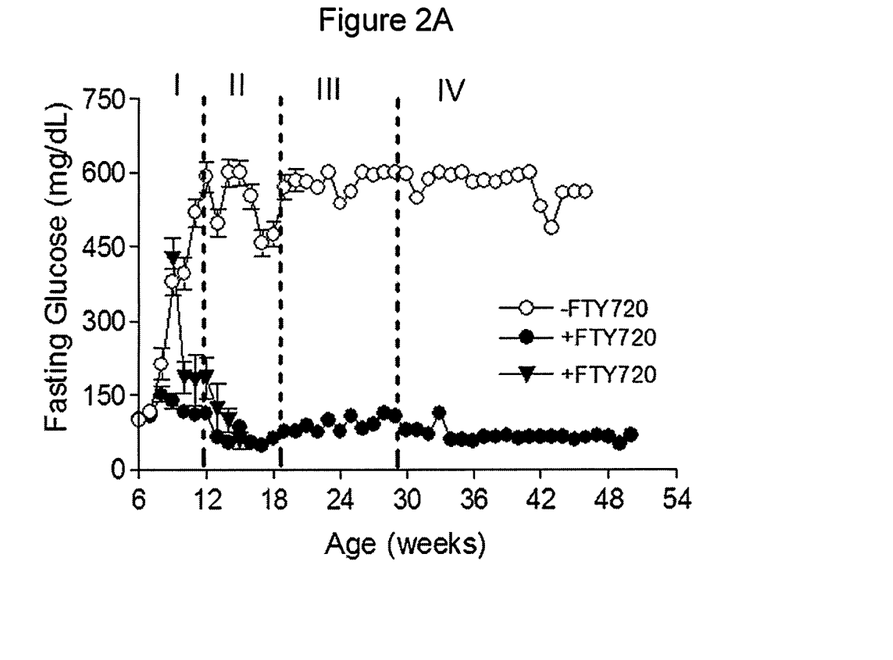
Figure 2B:
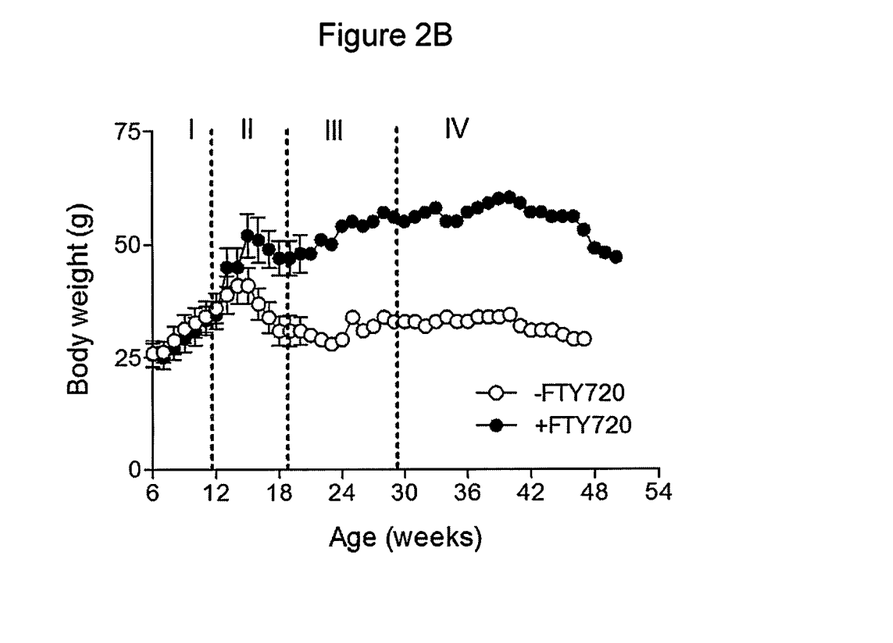

Importantly, this well controlled fasting glucose levels over time occurred despite the fact that FTY720 administration was ceased completely after 29-weeks treatment (FIG. 2A). In addition, weight gain, a common side effect of insulin therapy, was significantly higher in the FTY720-treated group than in the untreated group (FIG. 2B)

Figure 3:
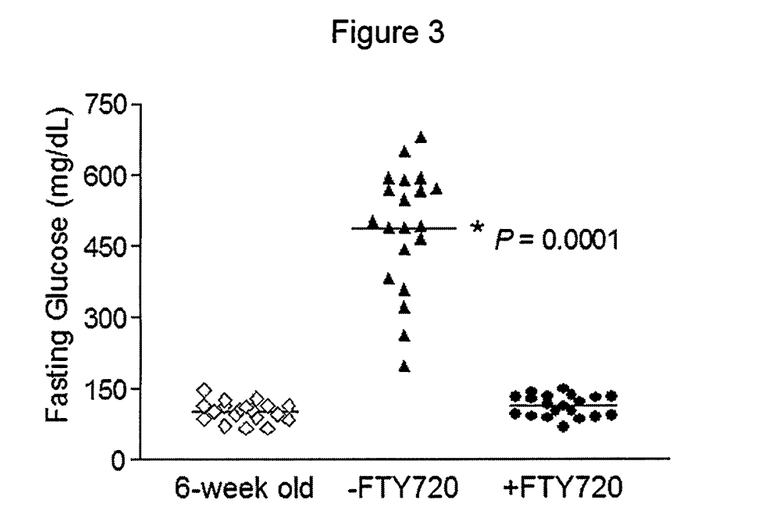
FIG. 3. The distribution of fasting glucose levels after 6 weeks treatment of FTY720. Open circle (◇), the db/db mice before treatment; triangle (▲), FTY720-untreated group; solid circle (●), FTY720-treated group (*p<0.0001, one way ANOVA-test).
Figure 4:
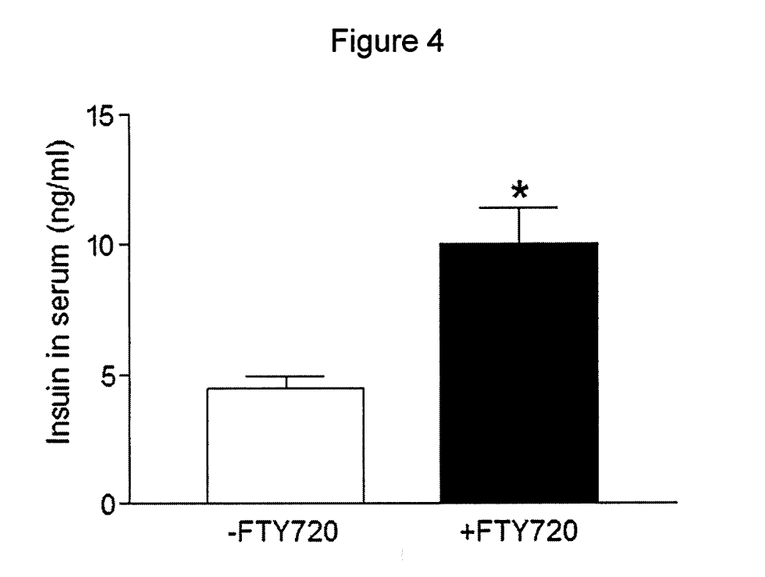
FIG. 4. Fasting serum insulin levels of the db/db mice with (+FTY720) or without FTY720 (−FTY720) treatment (*p<0.01).

Further examination of the distribution of fasting glucose as shown in FIG. 3 reveals that the fasting glucose levels in all FTY720-treated db/db mice were normalized. In addition, the blood insulin measurement also revealed that the fasting serum insulin levels were significantly elevated in the FTY720-treated group (FIG. 4). These data demonstrate that FTY720 can effectively control blood glucose levels within a relative normal range by increasing insulin levels in the db/db mice.

Figure 5A:
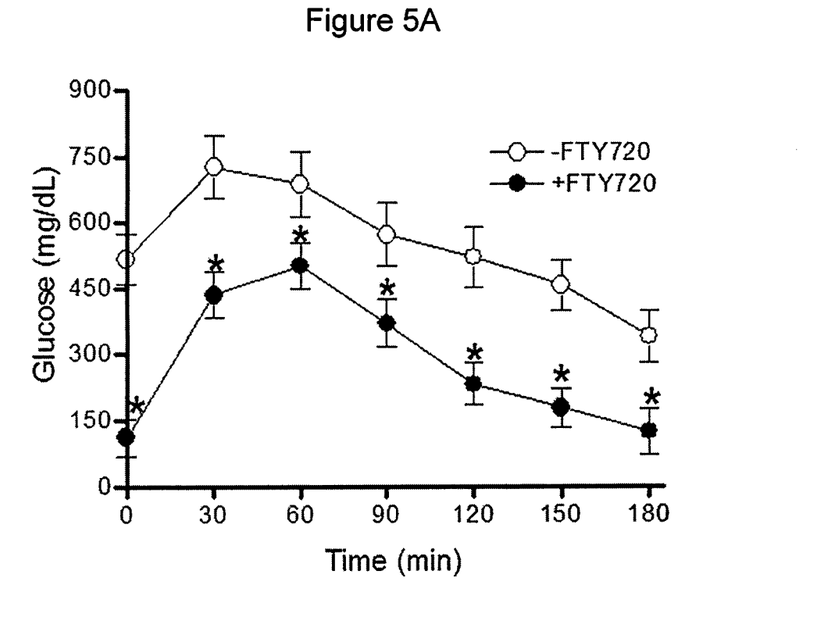
FIG. 5A. Intraperitoneal glucose tolerance test (GTT). The mice of both groups were fasted for 16 hours and intraperitoneally injected with 10% glucose (1 mg/g body weight). Glucose levels were then measured after 0, 30, 60, 90, 120 min by a Glucometer Elite (Bayer Corp., Elkhart, Ind.). Open circle (○), FTY720-untreated group; solid circle (●), FTY720-treated group. *p<0.01.
Figure 5B:
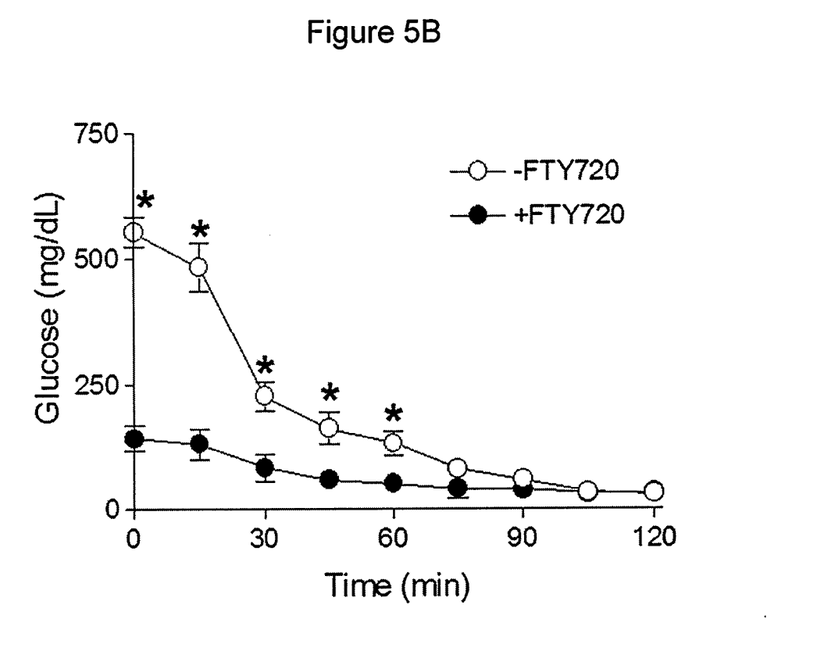
FIG. 5B. Insulin tolerance test (ITT). db/db mice with or without FTY720 treatment were fasted for 6 hours, and injected intraperitoneally with human regular insulin (0.55 U/kg) (Sigma), Tail blood samples were collected at 0, 30, 40, 60, 90, 120 min for glucose measurement. Open circle (○), FTY720-untreated group; solid circle (●), FTY720-treated group. *p<0.05.

In addition, glucose tolerance tests demonstrated the glucose tolerance was significantly improved in the FTY720-treated db/db mice as compared to that in the untreated mice (FIG. 5A), whereas insulin sensitivity was not affected as demonstrated by the insulin tolerance test (FIG. 5B). Specifically, initial fasting glucose levels in the untreated group were about 500 mg/dL but declined rapidly in the first hour after insulin administration; glucose levels in the treated and untreated groups were similar after 70 min (FIG. 5B). These data provide evidence that oral administration of FTY720 reversed the impaired glucose tolerance in db/db mice. Further these results indicate that administration of FTY720 to the db/db mice can normalize fasting blood glucose leading to prevention and reversal of diabetes without affecting insulin sensitivity.

Thus, the present invention provides methods of treating a subject with prediabetes or with T2D comprising administering to a subject an effective amount of FTY720.

Example 2

FTY720 Treatment Increases Beta-cell Mass in db/db Mice

Figure 6:
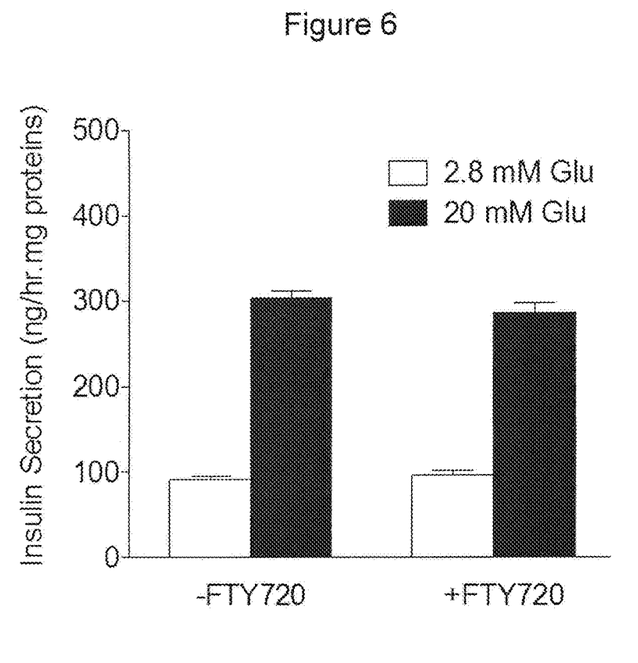
FIG. 6. FTY720 does not affect glucose-stimulated insulin secretion by normal islets ex vivo.

Islets were isolated from 8 weeks old normal C57/BL6 mice and treated with or without 0.2 µM FTY720 in the culture medium without FBA for 24 hours. Then the islets were stimulated with glucose and secreted insulin was measured using an Ultra Sensitive Mouse Insulin ELISA Kit (Crystal Chem Inc., Downers Grove, Ill.) and total proteins of islets were measured. FTY720 does not affect glucose-stimulated insulin secretion ex vivo in the isolated pancreatic islets (FIG. 6).

Figure 7:
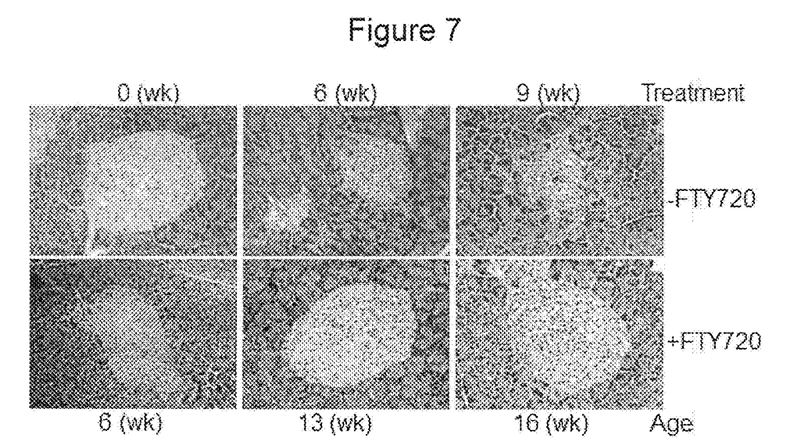
FIG. 7. Hematoxylin and eosin (HE) staining of pancreas from the FTY720-untreated and the treated mice. After 6 and 9 weeks of treatment, pancreases were removed from the db/db mice and embedded in paraffin. Paraffin sections (10 μm thick) were stained with HE and analyzed with a microscope (Scale bar, 50 μm).
Figure 8:
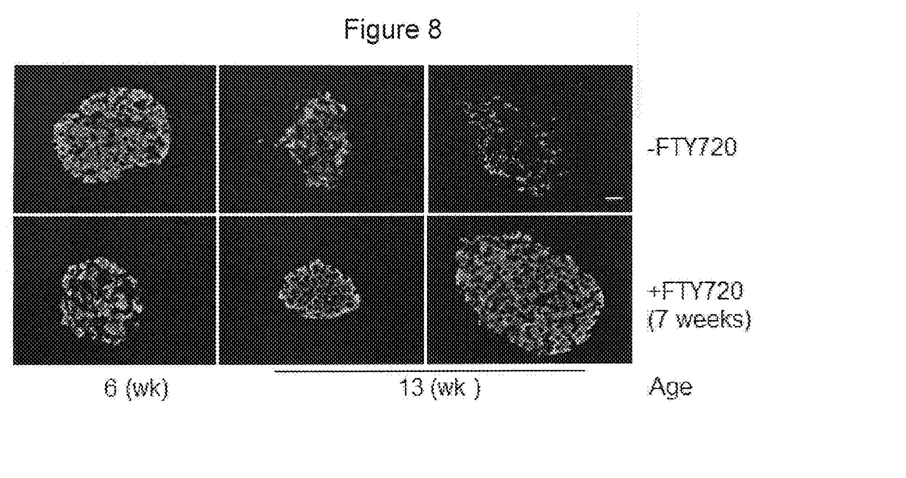
FIG. 8. Insulin immunostaining (green fluorescence) of the pancreatic islets. After 6 and 9 weeks treatment of FTY720, pancreases were removed from the db/db mice and embedded in paraffin. Paraffin sections (10 μm thick) were immunostained fluorescently for insulin (green color) (Scale bar 50 μm).
Figure 9:
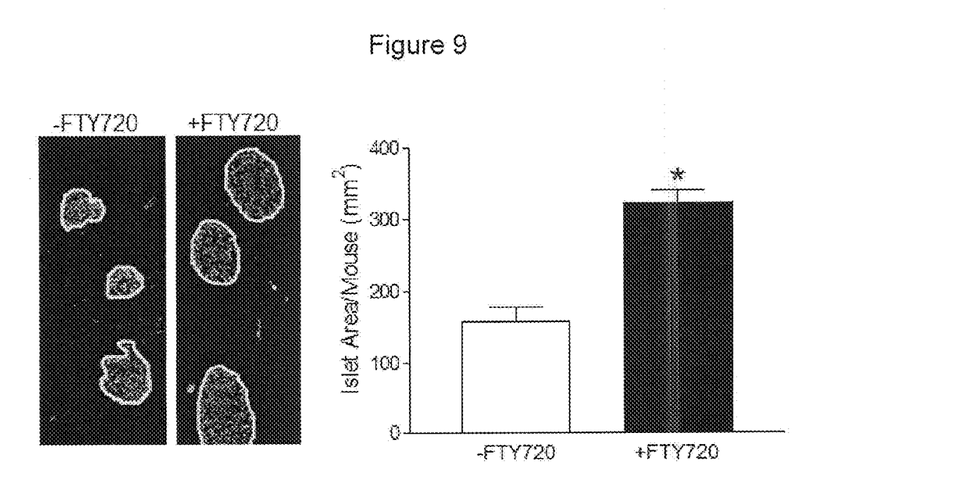
FIG. 9. Stereological quantification of the islet areas in the FTY720-untreated and the FTY720-treated db/db mice. Six consecutive paraffin sections (10 μm) from each pancreas (10 pancreases from the untreated and 9 from the FTY720-treatment db/db mice) were used for islet area measurements. *p<0.01.

Because FTY720 treatment increased fasting insulin levels in the db/db mice (FIG. 4) and did not affect the glucose-stimulated insulin secretion ex vivo (FIG. 7), the islet morphology, size and insulin content in pancreases were compared between the two groups of animals. Both hematoxylin and eosin (H&E) staining (FIG. 7) and immunohistochemical staining for insulin (FIG. 8) indicated that the untreated db/db mice experienced deterioration in islet morphology and a reduction in beta-cell mass over time. In contrast, the FTY720-treated group exhibited normal islet morphology (FIGS. 7 and 8). Stereological quantification also showed that pancreatic islets in these FTY720-treated mice were significantly larger than those in the untreated group (FIG. 9). Taken together, these results demonstrated that FTY720 treatment increased beta-cell mass and improved islet morphology in db/db mice.

FTY720 Treatment Increase Beta-cell Survival in db/db Mice

Figure 10A:
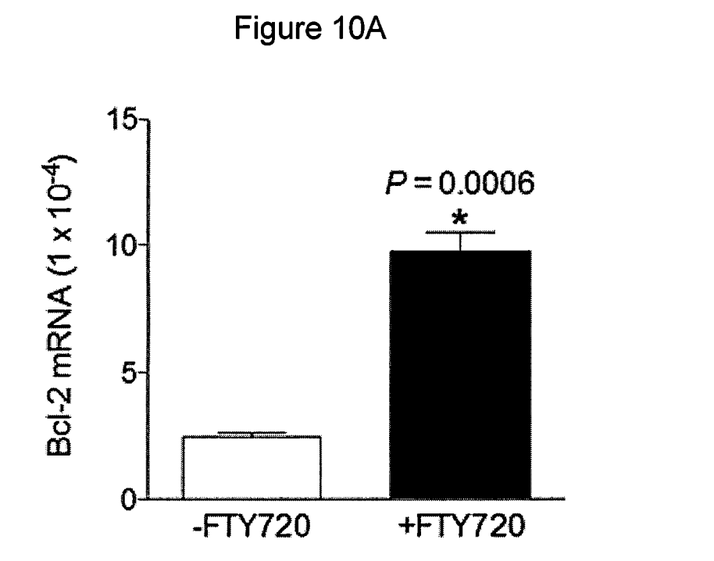
FIG. 10A. Levels of Bcl-2 mRNA levels of the db/db mice with (+FTY720) or without FTY720 (−FTY720) treatment. *p=0.0006
Figure 10B:
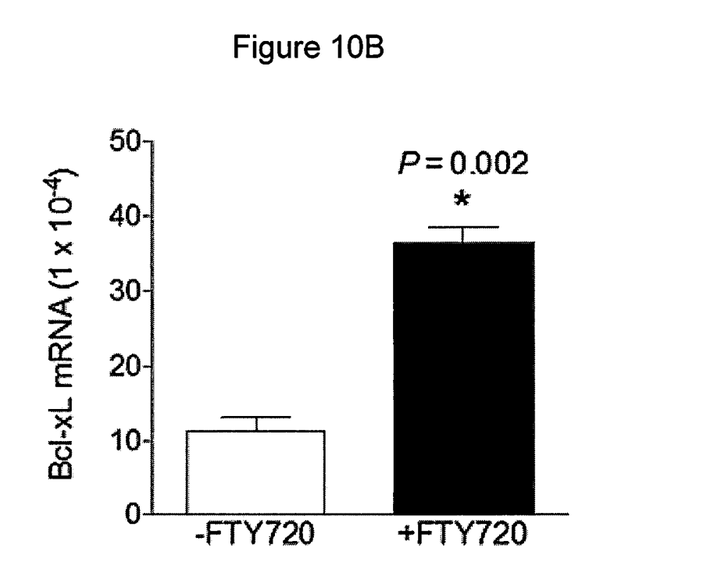
FIG. 10B. Levels of Bcl-xL mRNA levels of the db/db mice with (+FTY720) or without FTY720 (−FTY720) treatment. *p=0.002

To determine the mechanism of action (MOA) behind the increase in beta-cell mass observed in the treated mice, beta-cell survival was examined. Very few apoptotic beta-cells were observed in the pancreases of the untreated group, most likely due to the rapid clearance of apoptotic cells by phagocytes or adjacent cells in vivo. However, Bcl-2 (FIG. 10A) and Bcl-xL (FIG. 10B) were significantly increased in the islets from the FTY720-treated mice. These data suggest that islet cells in treated mice may have increased survival ability through up-regulation of Bcl-2 and Bcl-xL.

FTY720 Treatment Increases Beta-cell Proliferation in db/db Mice

Figure 11:
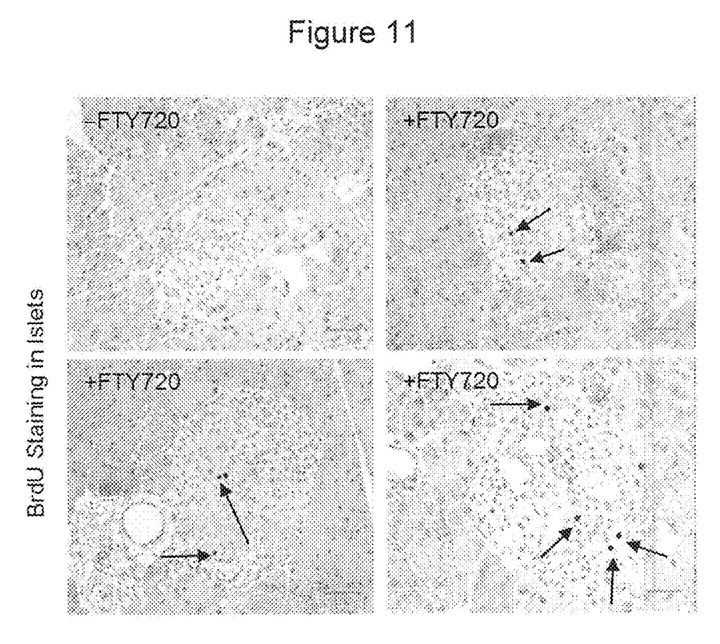
FIG. 11. BrdU staining in the pancreatic islets after 6 weeks FTY720 treatment. After overnight fasting, the mice were given 1 mg/ml 5-bromo-2'deoxyuridine (BrdU) intraperitoneally. 24 hours later, mice were sacrificed for BrdU staining of pancreas sections. Positive BrdU staining indicates cell proliferation. BrdU positive cells (brown) were observed in islets of the FTY720-treated mice (black arrows) (Scale bar, 100 μm).

The degree of beta-cell in vivo proliferation in islets from the two groups of animals was determined by the in vivo BrdU incorporation experiments. There was no BrdU staining in the pancreas section prepared from the untreated mice; however, BrdU-positive cells were easily observed within the islets from the treated mice (FIG. 11), demonstrating that FTY720 induces beta-cell proliferation in the islets.

FTY720 Treatment Increases Beta-cell Neogenesis in db/db Mice

Figure 12:
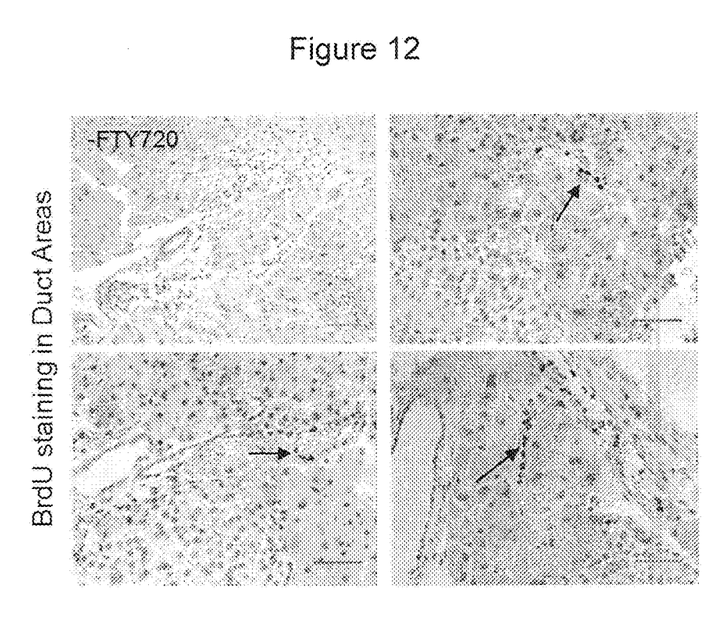
FIG. 12. BrdU staining in the duct areas of the pancreas. After 6 weeks FTY720 treatment, overnight fasted mice were given 1 mg/ml 5-bromo-2'deoxyuridine (BrdU) intraperitoneally. 24 hours later, mice were sacrificed for BrdU staining of pancreas sections. BrdU positive cells (brown) were observed in the duct area in the pancreas of FTY720-treated mice (Scale bar, 100 μm).
Figure 13:
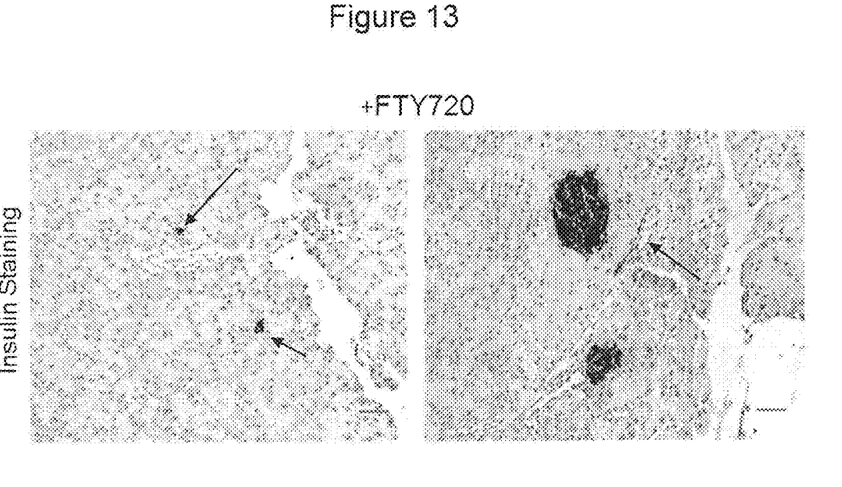
FIG. 13. Insulin immunostaining in newly formed insulin containing cells and islets near duct (arrow) in the FTY720-treated db/db mice (Scale bar, 100 μm).

It has been suggested that new beta-cells may arise from the proliferation of pancreatic progenitor cells located in the ductal lining. Therefore, the in vivo BrdU incorporation was examined in the pancreatic duct area. No BrdU staining was detected in the islets and ductal lining of the untreated mice (FIG. 12). In vivo BrdU incorporation was observed in the pancreatic duct area of the FTY720-treated mice (FIG. 12). These data evidence that oral administration of FTY720 to db/db mice stimulated beta-cell neogenesis in the pancreatic duct area. Interestingly, the insulin-positive cells or small islets were also identified in the pancreatic duct area of the treated mice (FIG. 13) providing evidence that oral administration of FTY720 to db/db mice stimulated new insulin producing cell regeneration. Together, these data indicated that FTY720 induces in-vivo beta-cell regeneration in db/db mice.

Thus, the present invention provides a method of stimulating insulin producing beta-cell proliferation and regeneration in vivo in a subject with prediabetes and with T2D comprising administering to subject an effective amount of FTY720.

Experiment 3

FTY720 Treatment Activates PI3K Signaling Pathway in db/db Islets

Figure 14:
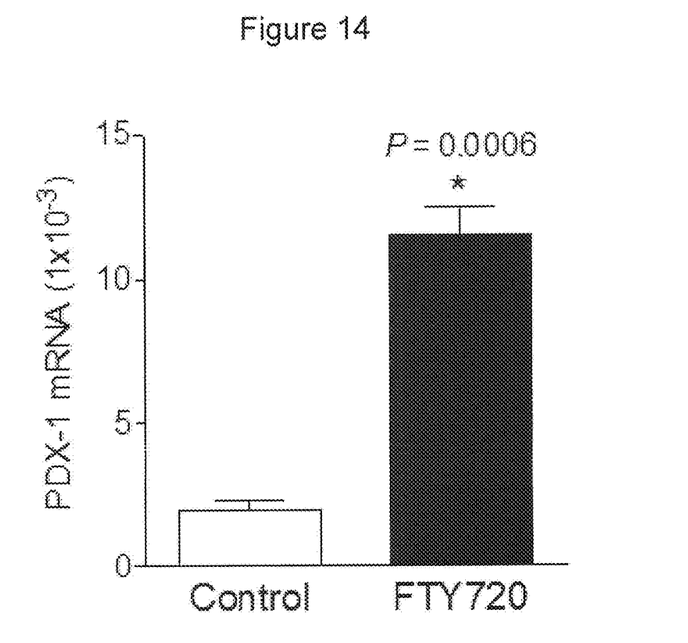
FIG. 14. PDX-1 expression in the isolated islets from the db/db mice with (+FTY720) or without FTY720 (−FTY720) treatment (*p=0.0006).

Expression of pancreatic and duodenal homeobox (PDX-1), a transcription factor, is required for pancreatic development and β-cell maturation. This invention demonstrated that the PDX-1 expression in the islets from the FTY720-treated db/db mice was 6-fold higher than that in the islets from the untreated mice consistent with PI3K activation (FIG. 14). These data provide evidence that oral administration of FTY720 significantly increases the expression of pancreatic and duodenal homeobox 1 (PDX-1) in the islets of the db/db mice.

Experiment 4

FTY720 Treatment Up-regulates SIP Receptors in db/db Islets

Figure 15:
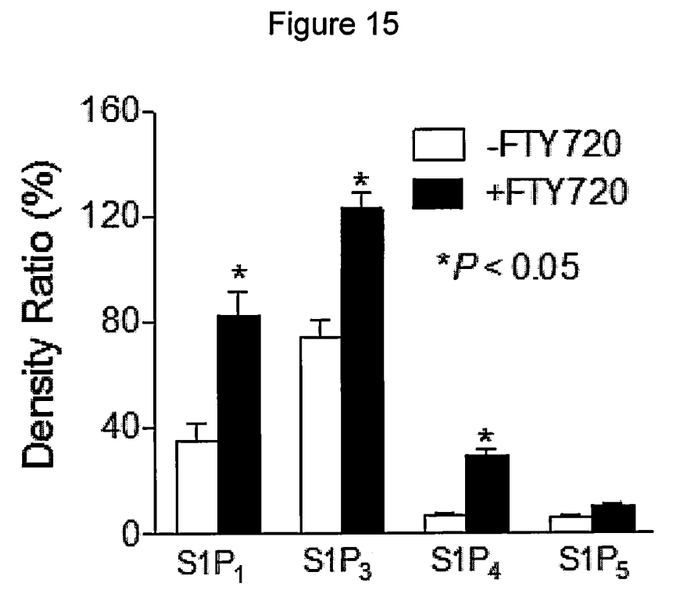
FIG. 15. Expression of 4 FTY720-bound S1P receptors in the islets isolated from the db/db mice.

FTY720 is phosphorylated in vivo to form FTY720-P that binds $S1P_1$, $S1P_3$, $S1P_4$, and $S1P_5$ but not $S1P_2$ (25). We determined the expression of these receptors in the islets isolated from the untreated and FTY720-treated db/db mice. As shown in FIG. 15, $S1P_3$ were predominantly expressed in the db/db islets whereas $S1P_4$ and $S1P_5$ were hardly detected. However, after FTY720 treatment of db/db mice, $S1P_1$, $S1P_3$, and $S1P_4$ but not $S1P_5$ were significantly elevated in the islets. These data provides evidence that $S1P_3$ expression is highest one among four FTY720-bound S1P receptors in the islets of the db/db mice and is further elevated by FTY720 treatment.

It is well documented that FTY720 is phosphorylated in vivo to form FTY720-P that binds to $S1P_1$ and induces $S1P_1$ downregulation and desensitizes $S1P_1$ signaling, which prevents lymphocyte egress from lymphoid tissues. In fact, S1P3 expression is the highest one among four FTY720-P bound receptors in db/db mouse islets. It is likely that the activity of FTY720-P lies in its activity at $S1P_3$ that has been shown to play an important role in promoting cell survival and proliferation. Thus, the present disclosure provides a possible mode of action for FTY720 for its ability to stimulate insulin producing beta-cell proliferation and regeneration in vivo in a subject with prediabetes or with T2D.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teaching of the invention without departing from essential scope thereof. Therefore, it is intended that the invention not be limited by the above described embodiments, methods, and examples, but by all embodiments and methods within the scope and spirit of the invention as claimed.

What is claimed is:

1. A method for treating a subject having type-2 diabetes comprising administering to the subject, a composition consisting essentially of an effective amount of 2-amino-2-[2-(4-octylphenyl)ethyl]propane-1,3-diol (FTY720) or a pharmaceutically acceptable salt thereof, or 2-amino-2-(hydroxymethyl)-4-(4-octylphenyl)butyl dihydrogen phosphate (FTY720-P) or a pharmaceutically acceptable salt thereof.

2. A method for preserving or increasing the mass of functional beta-cells in a subject having type-2 diabetes comprising administering to the subject a composition consisting essentially of an effective amount of FTY720 or a pharmaceutically acceptable salt thereof, or FTY720-P or a pharmaceutically acceptable salt thereof.

3. A method for increasing insulin levels in a subject having type-2 diabetes comprising administering to the subject a composition consisting essentially of an effective amount of FTY720 or a pharmaceutically acceptable salt thereof, or FTY720-P or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 8,653,026 B2 |
| APPLICATION NO. | : 13/722495 |
| DATED | : February 18, 2014 |
| INVENTOR(S) | : Zhongmin Ma |

It is certified that error appears in the above-identified patent and that said Letters Patent is hereby corrected as shown below:

On the title page, item (72) Inventor, delete "Zhonigman" and replace with "Zhongmin".

Signed and Sealed this
Fifth Day of August, 2014

Michelle K. Lee
*Deputy Director of the United States Patent and Trademark Office*